United States Patent [19]

Lituchy

[11] Patent Number: 5,205,829
[45] Date of Patent: Apr. 27, 1993

[54] SAFETY DISPOSABLE INTRAVENOUS (I.V. ASSEMBLY)

[76] Inventor: Andrew E. Lituchy, 50 Columbus Ave., Apt. 618, Tuckahoe, N.Y. 10707

[21] Appl. No.: 477,625

[22] Filed: Feb. 9, 1990

[51] Int. Cl.⁵ .............................................. A61M 5/00
[52] U.S. Cl. .................................. 604/164; 604/263; 604/264
[58] Field of Search ............... 604/162, 163, 165, 171, 604/177, 192, 198, 110, 263, 164, 264

[56] References Cited

U.S. PATENT DOCUMENTS

| | | | |
|---|---|---|---|
| 4,026,287 | 5/1977 | Haller | 128/215 |
| 4,170,993 | 10/1979 | Alvarez | 128/214 |
| 4,507,117 | 3/1985 | Vining et al. | 604/196 |
| 4,563,176 | 1/1986 | Gustavsson et al. | 604/163 |
| 4,592,744 | 6/1986 | Jagger et al. | 604/192 |
| 4,659,330 | 4/1987 | Nelson et al. | 604/192 |
| 4,675,005 | 6/1987 | DeLuccia | 604/110 |
| 4,685,905 | 8/1987 | Aab | 604/247 |
| 4,692,155 | 9/1987 | Dimmer | 604/177 |
| 4,692,156 | 9/1987 | Haller | 604/195 |
| 4,695,274 | 9/1987 | Fox | 604/198 |
| 4,710,170 | 12/1987 | Haber et al. | 604/110 |
| 4,735,618 | 4/1988 | Hagen | 604/192 |
| 4,747,830 | 5/1988 | Gloyer et al. | 604/110 |
| 4,762,516 | 8/1988 | Luther et al. | 604/164 |
| 4,772,264 | 9/1988 | Cragg | 604/158 |
| 4,790,828 | 12/1988 | Dombrowski et al. | 604/198 |
| 4,790,829 | 12/1988 | Bowden et al. | 604/244 |
| 4,834,718 | 5/1989 | McDonald | 604/195 |
| 4,846,192 | 7/1989 | MacDonald | 128/752 |
| 4,917,669 | 4/1990 | Bonaldo | 604/164 |
| 4,950,252 | 8/1990 | Luther et al. | 604/164 |
| 5,000,740 | 3/1991 | Ducharme et al. | 604/198 |
| 5,092,845 | 3/1992 | Chang | 604/164 |

Primary Examiner—C. Fred Rosenbaum
Assistant Examiner—William Lewis
Attorney, Agent, or Firm—Hedman, Gibson & Costigan

[57] ABSTRACT

An intravenous catheter which protects a clinician from accidental puncture from needle stick injuries which may result in the dangerous transfer of infectious diseases is disclosed which is easily operated with one hand and is compact for easy disposal.

2 Claims, 5 Drawing Sheets

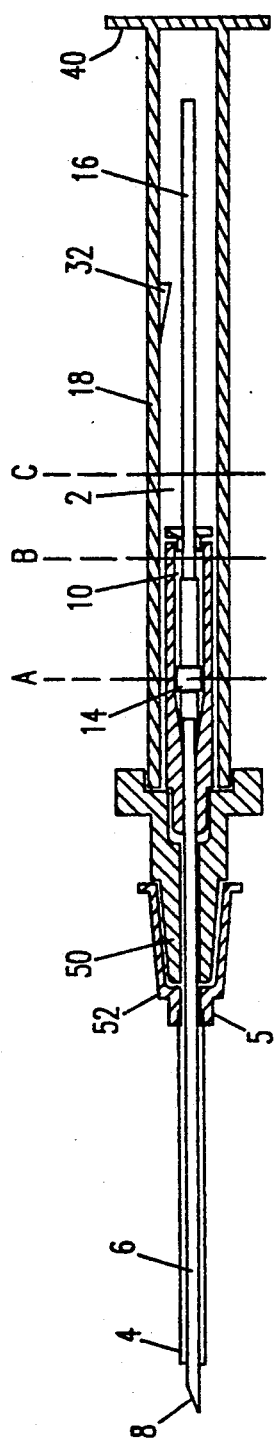
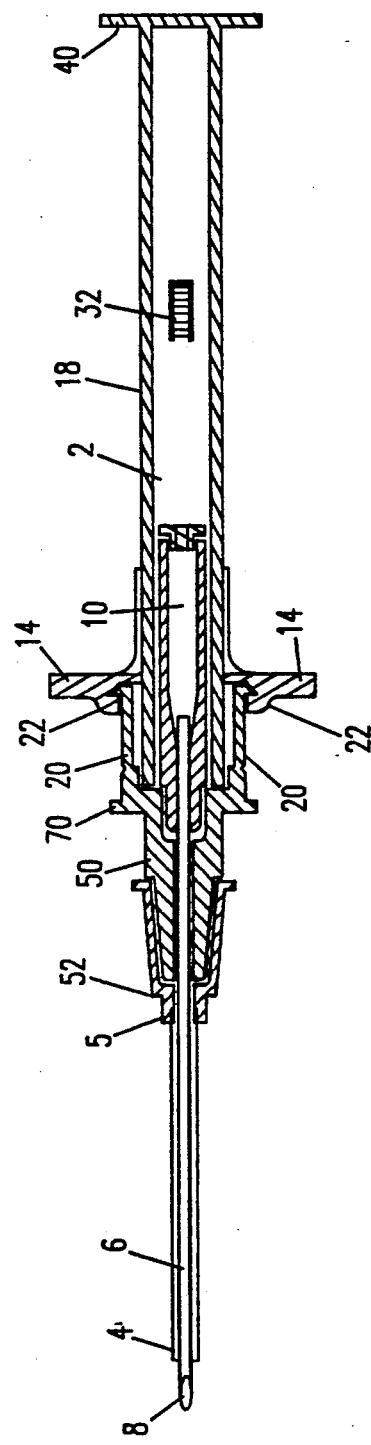
FIG. 1
FIG. 2

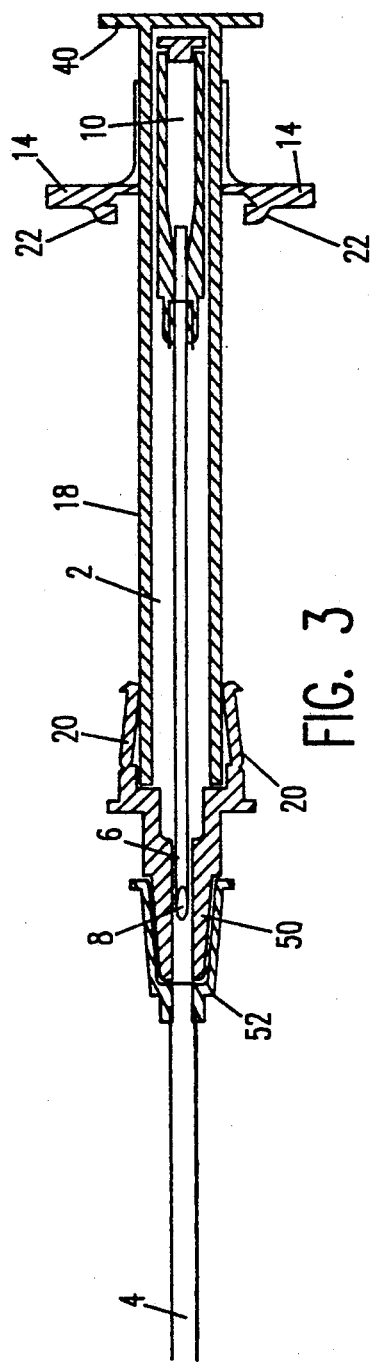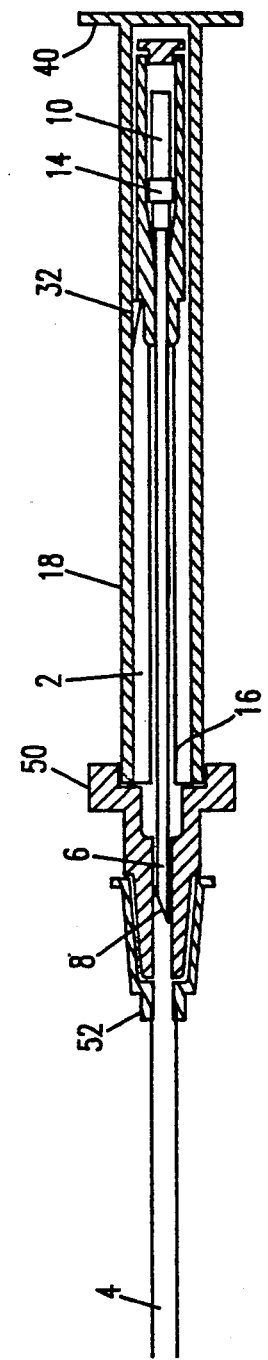

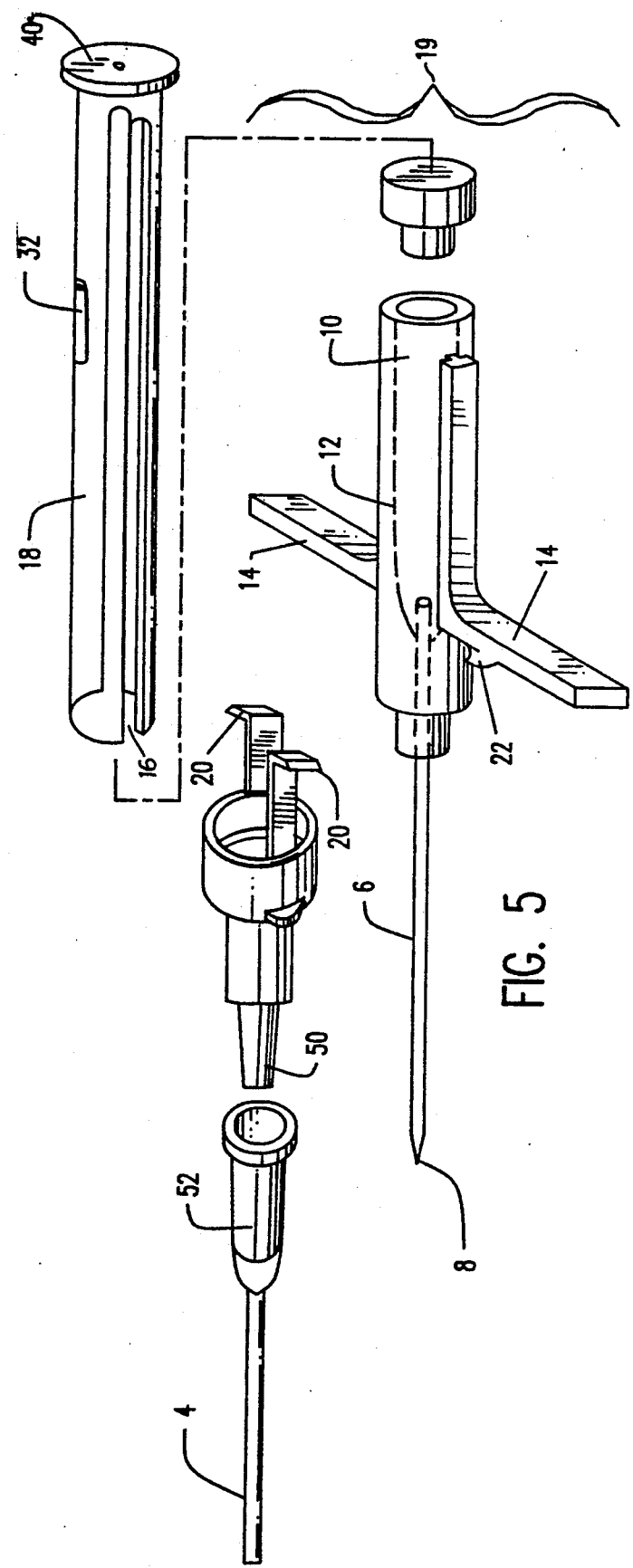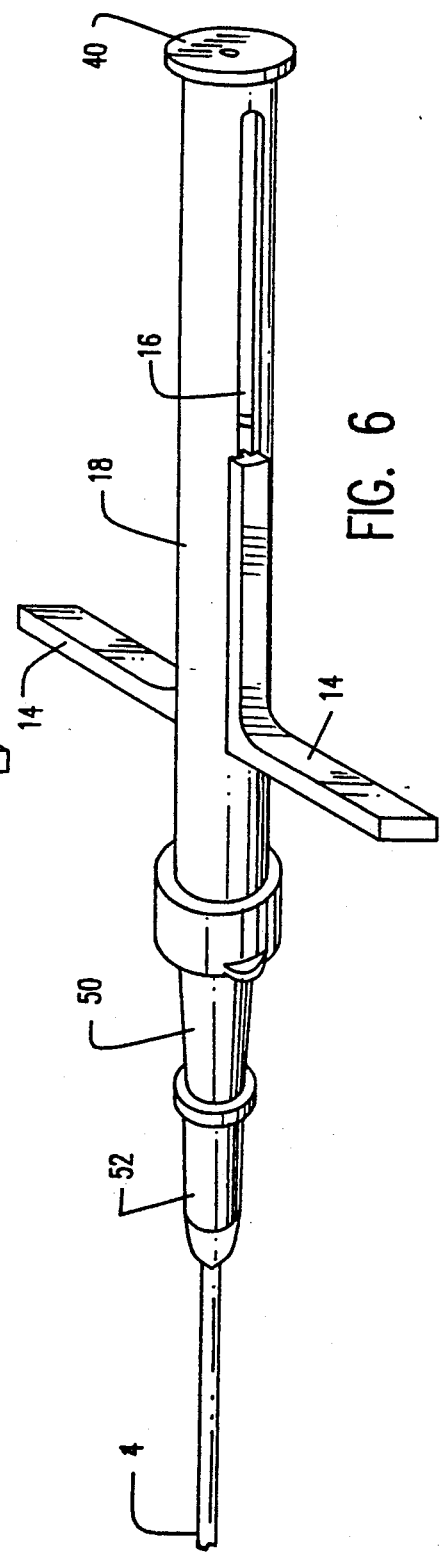

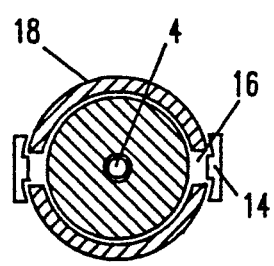
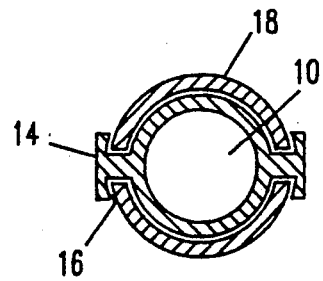
FIG. 7    FIG. 8
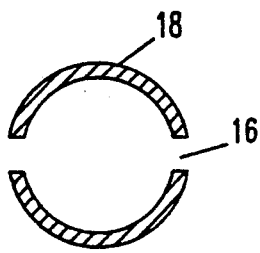
FIG. 9
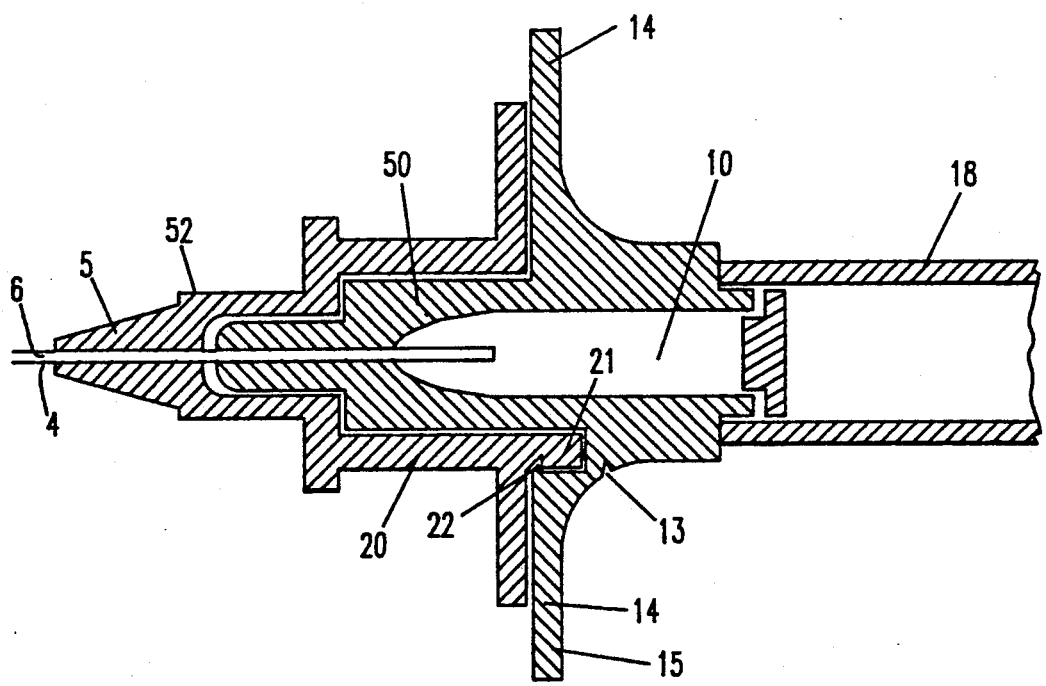
FIG. 13

SAFETY DISPOSABLE INTRAVENOUS (I.V. ASSEMBLY)

The present invention relates to an apparatus useful in puncturing the skin of a patient to be treated with a fluid, in particular an intravenous (I.V.) catheter assembly. More particularly, the present invention relates to a device which provides protection from needle stick injuries for the personnel using the device.

BACKGROUND OF THE INVENTION

In the medical health professions, a health hazard commonly known as the "needle stick" exists. The hazard exists because needles or cannula employed in the profession do not have safety features to prevent a used needle or cannula from accidentally sticking or puncturing the flesh of medical, clean up and/or other personnel before the used needle or cannula is finally disposed of.

The needle stick hazard, of course, incurs the possibility of transmitting infectious diseases such as hepatitis, AIDS, herpes and the like through needles or cannula which have become contaminated through prior usage.

A wide variety of devices in the prior art are designed to prevent needle stick injuries in the use of hypodermic needles. There are two basic types employed in this area. The first type may generally be described as an attached but retractable covering means or a sliding sheath. Typical of this embodiment are Fox, U.S. Pat. No. 4,695,274; Dombrowski, U.S. Pat. No. 4,790,828; Hagen, U.S. Pat. No. 4,735,618 and Nelson et al., U.S. Pat. No. 4,659,330.

The second type generally consists of a plunger or piston which operates to both expulse medicament and to selectively engage the needle carrying base to relocate the needle inside the syringe upon withdrawal of the plunger or piston. These are described in, inter alia, Haber et al., U.S. Pat. No. 4,710,170; Vining et al., U.S. Pat. No. 4,507,117; DeLuccia, U.S. Pat. No. 4,675,005; Haller, U.S. Pat. No. 4,692,156 and Gloyer et al., U.S. Pat. No. 4,747,830.

The prior art also describes devices aimed at preventing needle-stick injuries in intravenous catheters.

Jagger et al., U.S. Pat. No. 4,592,744 broadly describes safety venipuncture devices having a needle retracting means, which may include intravenous devices as well as hypodermic needles and vacuum tube phlebotomy systems. The patentee generally teaches a needle retracting means comprising withdrawing a hub located at the rear of the device, which is also connected to the needle assembly. Thus, upon withdrawing the hub, the needle assembly is relocated to a protected interior portion of the device.

McDonald, U.S. Pat. No. 4,834,718 discloses an intravenous catheter apparatus designed to aid in protecting a clinician from accidental puncture. The patentee teaches a means for withdrawing the needle from a patient's body into a protective housing without exposing the needle during any intermediate stage of the process. A handle means, located at the rear of the device, which is secured to the needle for manually pushing the needle forward to effect the puncture and thereafter for pulling the needle rearwardly in order to withdraw it from the puncture site into a protective housing.

Similarly, Luther et al., U.S. Pat. No. 4,762,516 disclose a needle catheter protector wherein the needle assembly is withdrawn into a protective housing by retracting an outer portion of the housing to which the needle is attached, so that the needle is locked within a forward bore element.

All of the above catheter protectors suffer from the need to withdraw the needle from a means located at the rear of the device. This rearward means requires the user to employ two hands to withdraw the needle into the protective housing. While one hand is on the housing and the other is withdrawing the needle from the rear of the device, the needle is likely to be moved and can either puncture the rear wall of the vein or slip out of the vein. In either instance, the whole process of inserting the catheter must be repeated. It would therefore constitute a notable advance in the state of the art if a safety catheter could be developed in which the withdrawal means could be operated with one hand, leaving the second hand free to ensure that the needle remains securely in the vein during withdrawal.

Furthermore, the use of a housing or sliding sheath removal means located at the rear of device presents disposal problems. All of the prior art safety catheters teach a device which when the needle is retracted is twice as long as the device when the needle is not retracted, due to the use of a sliding sheath to withdraw the needle. In this day and age of concern about and the expense of disposing of hospital waste, particularly needles, it is highly desirable to produce a more compact and easily disposable safety catheter.

Also to be mentioned is Alvarez, U.S. Pat. No. 4,170,993 which describes an intravenous assembly designed to aid in the emplacement of the needle within the patient's blood vessel.

SUMMARY OF THE INVENTION

It is therefore the object of the present invention to provide a disposable venipuncture apparatus which protects the use from needle stick injuries.

It is another object of the present invention to provide a disposable catheter with a means for withdrawing and locking the needle safely inside a protective housing or chamber after use.

It is still another object of the present invention to provide a disposable catheter wherein the withdrawing and locking means can be manipulated with one hand.

It is still a further object to provide a disposable catheter which remains compact after the needle has been withdrawn and is locked inside the protective housing or chamber.

Accordingly, the present invention provides a clinical disposable safety device comprising a needle having a pointed forward end adapted to puncture the skin of a patient. A handle means is secured to the needle rearwardly of the pointed end, and is adapted to traverse rearwardly along a slot contained in a protective housing means. In this manner the clinician or operator may manually withdraw the needle into the protective housing in a manner such that the pointed end is continuously protected from exposure to accidental puncture from the time of withdrawal from the catheter.

BRIEF DESCRIPTION OF THE DRAWINGS

FIG. 1 is a longitudinal sectional view of an I.V. catheter apparatus in accordance with the present invention, with the needle in the forward position.

FIG. 2 is a longitudinal sectional view of an I.V. catheter apparatus in accordance with the present invention, rotated 90° from FIG. 1, with the needle in the forward position.

FIG. 3 is a longitudinal sectional view of an I.V. catheter apparatus in accordance with the present invention, with the needle in the retracted position.

FIG. 4 is a longitudinal sectional view of an I.V. catheter apparatus in accordance with the present invention, rotated 90° from FIG. 3, with the needle in the retracted position FIG. 5 is a longitudinal exploded view of the apparatus of the present invention showing the component elements thereof.

FIG. 6 is a longitudinal sectional view of an I.V. catheter apparatus in accordance with the present invention, with the needle in a partially retracted position.

FIG. 7 is a cross-sectional view of an I.V. catheter apparatus in accordance with the present invention, at point A—A of FIG. 1.

FIG. 8 is a cross-sectional view of an I.V. catheter apparatus in accordance with the present invention, at point B—B of FIG. 1.

FIG. 9 is a cross-sectional view of an I.V. catheter apparatus in accordance with the present invention, at point C—C of FIG. 1.

FIG. 13 shows an alternative mechanism for locking the handle means in the forward position.

DETAILED DESCRIPTION OF THE PREFERRED EMBODIMENTS

Figure 10:
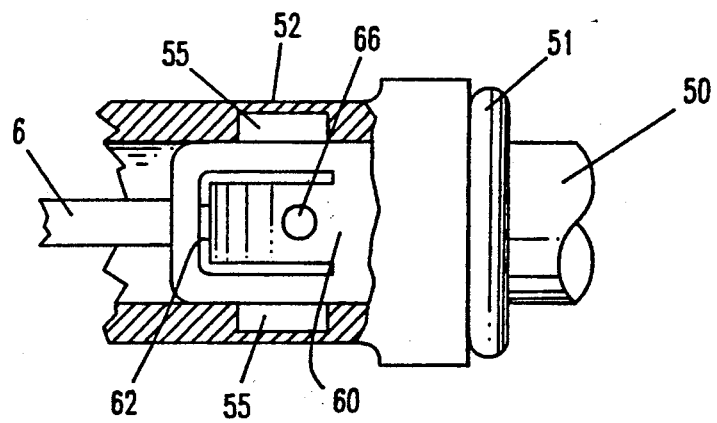
FIG. 10 is an enlarged cutaway view illustrating a locking mechanism incorporated into the apparatus of the preceding figures.

I.V. catheters are used millions of times a year in hospitals and clinics. They are necessary for the administration of fluids, blood, blood products and many medications. They often must be started rapidly in emergencies and they represent one of the most commonly used medical devices. Prevention of needle stick injuries has recently become an important issue in the use of catheters.

Needle stick injuries are probably the most common preventable injuries which threaten health care workers. The human and economic cost of such injuries is quite high. The rising concern over needle stick injuries reflects the fear of spreading infectious diseases, in particular, Human Immunodeficiency Virus (HIV) or AIDS, and hepatitis. Once a needle has been used, it becomes contaminated with the patient's blood and becomes a potential vector for the spread of disease. The Center for Disease Control (CDC) recommends that needles are not recapped after their use since this is the most common way that people are injured. Furthermore, it is required by law that needles and other sharp objects are disposed of in special puncture resistant containers. The used needles, of course, must be carried to these containers and pose a threat to the carrier if the pointed end is exposed. The dangers are substantially greater if the situation is an emergency and there are many people running about.

Additionally, besides the obvious health hazards, needle stick injuries incur a large financial liability. There is the direct cost of testing the patient for transmittable diseases, and often the injured employee requires prophylactic treatment as well as repeated testing for HIV, hepatitis and the like. If the worker does in fact contract a disease, the worker will also require extensive medical treatment. Finally, there is the potential liability for injury, pain and suffering and even wrongful death. The health care system must adsorb all of these costs.

FIGS. 1-9 show an intravenous catheter assembly generally designated 2 which comprises a catheter sheath 4 around a needle 6. The I.V. is inserted into a patient (not shown) by puncturing the skin of the patient with a pointed end 8 of needle 6. The needle 6 and catheter sheath 4 are introduced into the patient's vein in a manner known to those skilled in the art. When the flash-back of blood is noted in the flashback well 10, preferably comprising a magnifying means 12 on the sidewall of the needle assembly 19, this signals that the needle 6 has entered the vein. At this point, it is preferred to advance the I.V. about another 5 mm into the vein to allow the catheter sheath 4 to enter the lumen of the vein.

Once the catheter sheath 4 is securely within the vein of the patient, the clinician or operator withdraws the needle 6 by pulling back on the handle means. Preferably the handle means comprises wing or wings 14 which are connected to the base of needle assembly 19. The wing or wings 14 are adapted to traverse rearwardly along a slot 16 located along the length of protective housing means 18. In a preferred embodiment, in order to withdraw the wings 14, a locking mechanism 20 must be squeezed to release latch 22 located on wing 14. Alternatively, as shown in FIG. 13, the locking mechanism 20 may be operatively released from handle means 14. In this preferred embodiment, wing 14 is equipped with a recess 13 to enable wing 14 to bend backwards when pressure is placed on the outer portion 15 of wing 14. When wing 14 is pressed backward, latch 22 is released from flange 21 of locking mechanism 20 thereby allowing the handle means 14 and needle assembly 19 to traverse rearwardly along slot 16. Such locking means may be constructed on one or both wings. The catheter sheath 4 may then be fully advanced into the vein with the I.V. assembly still attached to the catheter hub 5.

When the wings 14 are fully withdrawn, the needle 6 is completely enclosed by the protective housing means 18. The protective housing means 18 may be molded of any clear plastic material. Especially preferred are polystyrene and polycarbonate. The protective housing means 18 is of course of sufficient length to accommodate the entire needle assembly when the handle means 14 is completely withdrawn. Further, the protective housing means 18 is also of sufficient thickness such that it is impossible for the needle to pierce through the side walls of the protective housing means 18.

In a preferred embodiment, when the wings 14 are fully withdrawn, the needle 6 is automatically locked into the protective housing means 18 by a locking device. The locking device preferably comprises wedges 32 and 34 which are molded into the inside wall of the protective housing means 18. Alternatively, the locking device may comprise any latch type lock known to those skilled in the art or a friction lock which comprises a protective housing means 18 having slightly smaller diameter at the end of the housing whereby the needle assembly base is held in place by friction. The cartridge with locked needle assembly 19 is then removed from the catheter fitting 52 and may be safely placed down while the I.V. tubing is inserted and secured with tape.

The catheter is entirely conventional and may be comprised of a wide variety of materials. Thus, expandable hydrophilic polymers, teflon, pvc, polyurethane, nylon, etc. all are available. Moreover a wide range of needle size may be utilized in the device and preferably ranges from about 12 to about 26 gauge.

In a preferred embodiment, the protective housing means 18 comprises a guard means 50 adapted to extend into abutment with the catheter fitting 52 in such a manner that the protective housing means 18 and the catheter fitting 52 form a continuous passageway such that rearward withdrawal of the needle assembly 19 from the catheter fitting 52 causes the pointed end 8 to be received within the protective housing means 18 no later than the time when it exits from the catheter fitting 52. Thus the pointed end 8 is continuously protected from exposure to accidental puncture from the time of withdrawal of the needle 6 from the catheter. Preferably the guard means 50 is a generally tubular body removably received within the catheter fitting 52 and affixed to the forward end of the protective housing means 18.

The guard means 50 and catheter fitting 52 may comprise a locking means 54 which locks the guard means 50 to catheter fitting 52 when the pointed end 8 of needle 6 extends inside the catheter fitting 52 and unlocks when the pointed end 8 is withdrawn from catheter fitting 52 so that the protective housing means 18 cannot be disconnected from the catheter fitting 52 until the pointed end 8 of needle 6 is withdrawn into the protective housing means 18.

Figure 11:
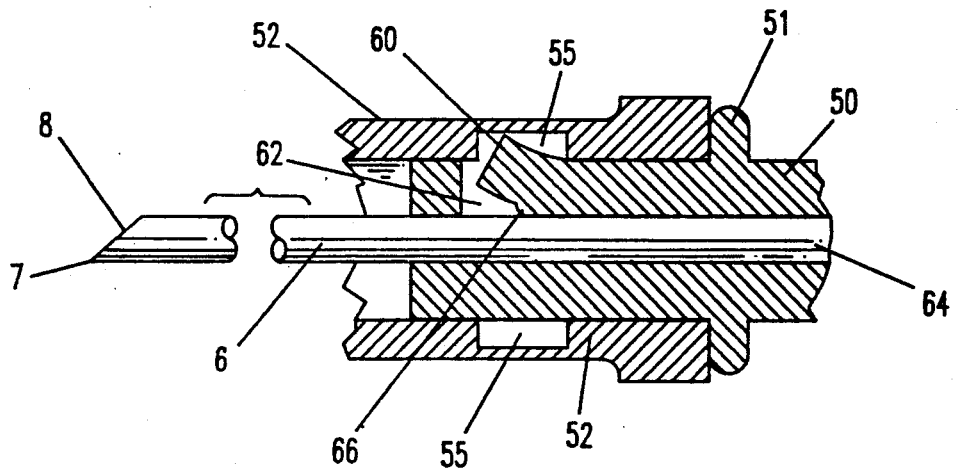
FIG. 11 is an enlarged sectional view taken along the line D—D of FIG. 10, illustrating the locking mechanism in its engaged position.

The locking means 54 may be any which are known to those skilled in the art. Preferably the locking means comprises a safety flange 51 formed on the outer surface of guard means 50 which abuts the rear of catheter fitting 52 and thereby prohibits further movement of the protective housing means 18. Locking tongue 60 is defined by a U-shaped opening 62 formed in the wall of guard means 50 near the forward end thereof as illustrated in FIG. 10. Locking tongue 60 is constructed to cooperate with annular recess 55 formed on the inner wall of catheter fitting 52. Opening 62 leaves tongue 60 connected at its rear end to the wall of guard means 50. It is inherently resilient and is biased to extend slightly radially inwardly. A boss 66 is located on the inner side of locking tongue 60. When the handle means 14 is in its forward position, as illustrated in FIGS. 1 and 2, needle 6 presses against boss 66 causing locking tongue 60 to be pushed radially outwardly into recess 64 of catheter fitting 52. The protective housing means 18 is thus locked to catheter fitting 52. See FIG. 11.

Figure 12:
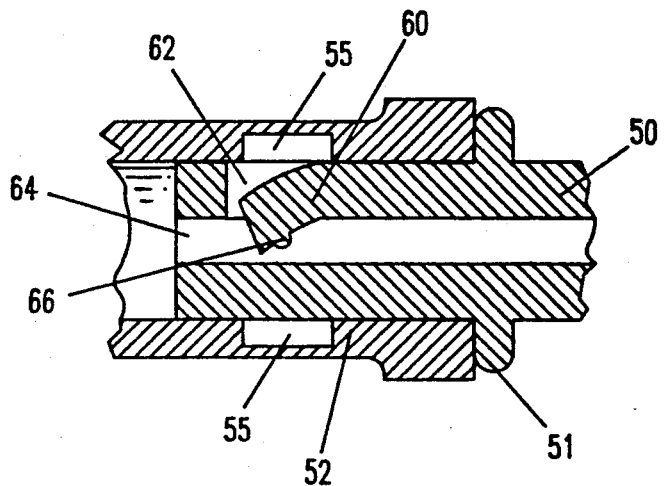
FIG. 12 is an enlarged view similar to FIG. 11, but illustrating the locking mechanism in its disengaged position.

When the handle means 14 is withdrawn rearwardly to the position illustrated in FIGS. 3 and 4, the rearward displacement of needle 6 provides clearance in passage 64 and allows locking tongue 60 to spring radially inward into the clearance in passage 64. The protective housing means 18 is then unlocked from catheter fitting 52. See FIG. 12. In the manufacture of the apparatus, needle 6 is preferably inserted into protective housing means 18 with the bevel 7 of the pointed end 8 facing away from boss 66 so as to avoid shaving off all or part of boss 66 during assembly.

It will be appreciated by those skilled in the art that the device of the present invention enables the clinician to employ only one hand in safely withdrawing the needle into the protective housing means, as opposed to the devices of the prior art wherein the needle withdrawal is effect from the rear of the device. In a preferred embodiment, the present device may also have a protective housing means having a widened rear for thumb placement to aid in one hand operation of the device.

The above mentioned patents are hereby incorporated by reference.

Many variations of the present invention will suggest themselves to those skilled in this art in light of the above detailed description. For example, any handle means, such as a knob or thumb placement, may be employed instead of the wing or wings. Any locking devices may be employed to lock the catheter fitting and protective housing means together, to release the needle assembly, and to secure the retracted needle assembly within the protective housing means.

Additionally the apparatus of the present invention may come equipped with a capping means over the needle and/or a capping means to fit over the guard means of the protective housing means. It is also contemplated to provide a gripping lip 70 to aid in steadying the device while withdrawing the needle assembly. It is further contemplated to use the device intra-arterial as well as intravenous. All such obvious modifications are within the full intended scope of the appended claims.

I claim:

1. A disposable safety needle apparatus comprising:
   (a) a needle assembly comprising a base and a needle having a pointed forward end adapted to intentionally puncture the skin of a patient;
   (b) a handle means secured to the needle rearwardly of said pointed forward end said handle means having at least one wing which extends substantially outwardly and further comprising a locking means for securing said handle means to said needle assembly which is released by pressing backward on an outer portion of said handle means to release a latch; and
   (c) a protective housing means for receiving the needle and having a slot contained therein adapted to enable said handle means to traverse rearwardly along the length of said protective housing means.

2. A disposable safety apparatus as defined in claim 1 further comprising:
   a catheter, one end of which is adapted to be inserted into a patient's blood vessel by means of said needle, and a catheter fitting secured to an opposite end of the catheter;
   whereby following insertion of the needle and catheter into a patient, rearward withdrawal of said needle from said catheter by said handle means is automatically effective to withdraw said needle assembly into said protective housing; the catheter and catheter fitting remaining with the patient; and the housing and enclosed needle assembly are separated from the catheter, catheter fitting and patient.

* * * * *